(12) United States Patent
Sun et al.

(10) Patent No.: US 10,702,264 B2
(45) Date of Patent: Jul. 7, 2020

(54) FIXING DEVICE FOR SOFT TISSUE

(71) Applicant: TransEasy Medical Tech.Co., Ltd, Beijing (CN)

(72) Inventors: Jie Sun, Beijing (CN); Hongjiu Qiao, Beijing (CN); Fan Chen, Beijing (CN); Lingcui Ding, Beijing (CN); Kai Meng, Beijing (CN)

(73) Assignee: TransEasy Medical Tech.Co., Ltd, Beijing (CN)

( * ) Notice: Subject to any disclaimer, the term of this patent is extended or adjusted under 35 U.S.C. 154(b) by 407 days.

(21) Appl. No.: 15/142,952

(22) Filed: Apr. 29, 2016

(65) Prior Publication Data

US 2016/0242766 A1    Aug. 25, 2016

(30) Foreign Application Priority Data

Jan. 25, 2016 (CN) .......................... 2016 1 0051764
Jan. 25, 2016 (CN) .......................... 2016 1 0051765
Jan. 25, 2016 (CN) .......................... 2016 1 0051818
Jan. 25, 2016 (CN) .......................... 2016 1 0051820
Jan. 25, 2016 (CN) ..................... 2016 2 0072770 U
Jan. 25, 2016 (CN) ..................... 2016 2 0073762 U

(51) Int. Cl.
*A61B 17/068* (2006.01)
*A61B 17/064* (2006.01)
*A61B 17/00* (2006.01)

(52) U.S. Cl.
CPC .......... *A61B 17/068* (2013.01); *A61B 17/064* (2013.01); *A61B 2017/00004* (2013.01); *A61B 2017/0084* (2013.01); *A61B 2017/00853* (2013.01); *A61B 2017/00889* (2013.01); *A61B 2017/0648* (2013.01); *A61B 2017/0649* (2013.01)

(58) Field of Classification Search
CPC ......... A61M 2039/1038; A61B 17/068; A61B 17/064; A61B 17/0682; A61B 2017/0648; A61B 2017/00853; A61B 2017/0649; A61B 2017/07235
See application file for complete search history.

(56) References Cited

U.S. PATENT DOCUMENTS 5,464,300 A * 11/1995 Crainich .............. A61B 17/068
                                                                403/322.1
2001/0009831 A1* 7/2001 Schink .................... A61L 15/18
                                                                442/123

(Continued)

*Primary Examiner* — Tan-Uyen T Ho
*Assistant Examiner* — Chima U Igboko

(57) ABSTRACT

A fixing device for soft tissue includes: a driving device, screw tube and a drive rod. A catheter is connected with the screw tube by screw thread, and a plurality of absorbable screws or titanium screws are provided in the catheter. A screw thread structure is formed on a nailed beam of each of the absorbable screws, and a lead spring is provided on each of the absorbable screws. The plurality of absorbable screws or titanium screws are connected in series and provided in the catheter with a spiral groove in a head-to-nail sequence. When used, by pulling the trigger, the driving rod is rotated driven by the driving device, in such a manner that the absorbable screw or the titanium screw can be shot out of the catheter one by one. The fixing device of the present invention has characteristics of anti-adhesion, convenient and reliable operation.

1 Claim, 3 Drawing Sheets

(56) References Cited

U.S. PATENT DOCUMENTS

| | | | | |
|---|---|---|---|---|
| 2003/0009441 | A1* | 1/2003 | Holsten | A61B 17/068 |
| 2004/0039304 | A1* | 2/2004 | Connors, III | A61M 25/01 |
| | | | | 600/585 |
| 2005/0251160 | A1* | 11/2005 | Saadat | A61B 17/0401 |
| | | | | 606/153 |
| 2009/0299294 | A1* | 12/2009 | Pinkus | A61M 25/02 |
| | | | | 604/177 |
| 2015/0133964 | A1* | 5/2015 | Ranucci | A61B 17/068 |
| | | | | 606/139 |
| 2016/0120557 | A1* | 5/2016 | Goddard | A61B 17/22 |
| | | | | 606/127 |
| 2016/0374684 | A1* | 12/2016 | DiNardo | A61B 17/068 |
| | | | | 227/179.1 |

* cited by examiner

1

FIXING DEVICE FOR SOFT TISSUE

CROSS REFERENCE OF RELATED APPLICATION

The present application claims priority under 35 U.S.C. 119(a-d) to CN 201610051820.2; CN201620072770.1; CN 201610051764.2; CN 201620073762.9; CN 201610051818.5; and CN 201610051765.7 which are all filed Jan. 25, 2016.

BACKGROUND OF THE PRESENT INVENTION

Field of Invention

The present invention relates to the technical field of mechanical equipments, and more particularly to a fixing device for soft tissue comprising an absorbable screw or a titanium screw.

Description of Related Arts

Incisional hernia, which refers to a type of hernia that abdominal viscera or tissue protrudes from abdominal incision, is a common placation in laparotomy. The incision along a middle line of a lower portion of the abdomen has a high incidence of incisional hernia. The incisional hernia mostly occurs on longitudinal incision positions of the abdomen including incision dehiscence, incision infection and a secondary incision healing. A minority of the incisional hernia appears a long time after operation on the ones without incision dehiscence history. A morbidity of the incisional hernia is at a range of 2-11%, and an infected incision has an incisional hernia of about 40%. The incisional hernia on abdominal wall is mainly treated by operation. The conventional repair method for the incisional hernia includes an open style hernia plastic operation with or without an artificial patch and a laparoscopicinc insional hernia repair operation. A recurrence rate of the incisional hernia by a simple tissue suture repair operation is up to 20-50%. According to a principle of incisional hernia classification in China, a medium-large or even huge scale of incisional hernia is more common in clinical trials. These types of incisional hernia are mainly performed with tension-free hernioplasty by artificial patch, which is capable of reducing the recurrence rate of the incisional hernia to about 10%. Compared with open style hernia plastic operations, the laparoscopicinc insional hernia repair has characteristics as follows.

(1) The laparoscopic incisional hernia repair follows the principle of abdominal wall hernia surgery, and is in line with biological engineering mechanics of repairing for strengthening the rear wall, and the recurrence rate after the operation is below 5%.

(2) The surgical approach is far away from the original incision hernia, so as to reduce the infection chance on implant positions of material, which is particularly suitable for the wound infection persons.

(3) A wide range of the abdominal tissue is not damaged to be free, and the original strength of the abdominal wall is retained as much as possible, which is more suitable for recurrent incisional hernia.

(4) Soft tissue capable of supplying blood is retained between skin on the hernia defect position and the artificial patch, and the soft tissue is capable of effectively cover and oppress the artificial patch, which is capable of facilitating the fibrous tissue to grow into an aperture of polypropylene mesh, so as to improve the tension strength between the artificial patch and the abdominal wall.

(5) Contents of free hernia in the pneumoperitoneum are more intuitively clear, and the force of gravity causes the contents of the hernia drooped naturally, so as to avoid the passive situation of intestinal injuries.

(6) An occult "pinhole hernia" is easier to find, so as to reduce the recurrence of abdominal hernia after operation caused thereby.

(7) Multi-point fixed patch is sutured and screwed in the abdominal cavity to reduce the uniformly dispersed tension.

(8) The area implanting the patch does has no skin incisions, so as to reduce the possibility of hematoma and liquid and replacement of a conventional drainage tube is not needed, so as to reduce the chance of contamination.

(9) The patch is fixed by non-abdominal wall penetration, so the postoperative pain is light, the duration of the operation is short and the patient recovers quickly.

(10) The laparoscopicinc operation is capable of not only reducing incisional infection, reducing postoperative recurrent rate but also achieving minimally invasive effects.

(11) The laparoscopicinc operation is technical demanding and requires a relative long learning time.

Based on the characteristics mentioned above, laparoscopic incisional hernia repair gradually attracts people's concern in recent years, and becomes more and more popular in the treatment of incisional hernia. The method for fixing patch in the laparoscopicinc hernia repair comprises completely suturing, completely nailing, combination of suturing, nailing and adhesive, and there is no uniform standard currently.

In the conventional art, TYCO healthcare group discloses a speculum stapling device and a disposable screw case in a patent application with an application number of 200810009395.6. In a US application with an application number of 2007/0038220 A1, John Isbell Shipp discloses an absorbable screw nail for fixing Surgical Mesh, wherein the absorbable screw nail is made of a copolymer of lactide and glycolide. In a US patent with an application number of US 2007/0250064 A1, Davol, Inc., Cranston, R.I. discloses a surgical operation fixing method and device. In a US patent with an application number of US 2003/0187465 A1, SOFRADIM PRODUCTION, Trevoux (FR) discloses an I-shaped operation fixing device. In a US application with a publication number of U.S. Pat. No. 5,366,479, Origin Medsystems, Inc. Menlo park, Calif. discloses a surgical spiral fixing device. The fixing device mentioned above solves the problems of time-consuming and inconvenient during the process of repairing suture, and furthermore, hemorrhage and trauma of the patient is decreased. The conventional surgical fixing device is in a type of a staple. Deformation fixed by the staple type fixing device needs other components such as an iron felt, and thus the structure is very complicated an the cost is high. A far-end of the one way screw nail has a penetrating point, and a near-end thereof has a T-shaped bar, wherein the T-shaped bar equally divides a diameter of the screw nail and provides a stress face. According to another embodiment, the screw nail is a double-sided screw, a far-end of the double-sided screw nail has two penetrating points and a near-end thereof has a connecting bar, wherein the connecting bar connects two spiral coils and equally divides diameters of the two spiral coils. In the conventional art, the fixing device is generally a disposable product and may cause friction tissue injury on the human body during operation process.

SUMMARY OF THE PRESENT INVENTION

In order to overcome the technical problems in the conventional art, the present invention provides a fixing device for soft tissue comprising an absorbable screw or a titanium screw.

Accordingly, in order to achieve the objects mentioned above, the present invention adopts technical solutions as follows.

A fixing device for soft tissue, comprising: a handle, an extension spring, a trigger, a driving gear, a large helical gear, a small helical gear, a screw tube and a driving rod;

wherein a first end of the extension spring is mounted on a fixing column on an internal wall of the handle, a second end of the extension spring is provided on an upper end of the trigger, a first side of the upper end of the trigger is rotatablely connected with an internal wall of the handle via a rotation axis;

a helical gear matching with the driving gear is provided on a second side of the upper end of the trigger, the trigger extends from an inside out of the handle, in such a manner that a lower end of the trigger is out of the handle;

the large helical gear and the driving gear are concentric, and the large helical gear is driven by the driving gear, external teeth of the large helical gear matches with external teeth of the small helical gear;

the driving rod is driven by the rotation axis of the small helical gear, the screw tube is sleeved on the driving rod, a first end of the screw tube is provided inside the handle, and a second end of the screw tube is provided out of the handle, a catheter is connected on the second end of the screw pipe by threaded connection, and an absorbable screw or a titanium screw is provided inside the catheter, a screw thread is provided on a nailed beam of the absorbable screw, and a lead spring is provided on the screw thread.

In the present invention, a lubricant coating comprising Teflon is covered on the catheter, and a thickness of the lubricant coating is at a range of 3-5 μm.

The fixing device for soft tissue, as recited in claim 2, wherein a surface hardness of the lubricant coating is at a range of Hv500-Hv1000, and a surface coefficient of friction is at a range of 0.1-0.05. The lubricant coating further comprises stable polymers selecting from a group consisting of: polymethyl methacrylate, polyacrylamide, polyacrylonitrile, polyether amide, Ethylenediamine, polycarbonate, polyketene, polyvinyl ether, polyvinyl ester, polyvinylpyrrolidone, polyethylene, polypropylene, polytetrafluoroethylene, polyolefin elastomer, polyisobutene, fluorosilicone, carboxymethyl chitosan, polyethylene terephthalate, polypentanoate, carboxymethyl cellulose, hydroxyethylcellulose, cellulose butyrate, cellulose acetate butyrate, ethyl-vinylacetate copolymer, chitosan and chitosan derivatives. Preferably, the lubricant coating further comprises antibacterial agent. Preferably, the lubricant coating comprises 0.01-1.5 wt % of antibacterial agent, wherein the antibacterial agent can be silver based antibacterial agent or non-silver based antibacterial agent. As an example of silver based antibacterial agent, the silver based antibacterial agent can be silver particles, silver based antibacterial agent or non-silver based antibacterial agent based on glass carriers, or silver based antibacterial agent based on zeolite carrier. The antibacterial agent can be added to a combination by a conventional mixing method and dispersed in a lubricating phase coating layer obtained by depositing. The antibacterial agent is capable of preventing or inhibiting growth of microorganisms carried, in such a manner that infection caused by fixing operation is prevented.

Preferably, the absorbable screw is made of degradable material. The degradable material is selected from a group consisting of: poly(L-lactide), poly(D, L-lactide), poly(L-lactide-co-D, L-lactide), poly(D,L-lactide-co-glycolide), poly-glycolide, poly(L-lactide-co-glycolide), poly(glycolide-co-trimethylene carbonate), poly(L-lactide-co-trimethylene carbonate), poly(D,L-lactide-co-trimethylene carbonate), poly(L-lactide-co-caprolactone), poly (amino acids), poly (ε-caprolactone), poly (δ-valerolactone), poly (γ-butyrolactone), poly (β-hydroxybutyrate), poly(DL-lactide), poly(L-lactide), ethylene carbonate (1,3-dioxolan-2-one), propylene carbonate (4-methyl-1,3-dioxolan-2-one), 1,3-propylene carbonate (1,3-dioxan-2-one) and tetramethylene carbonate (1,3-dioxacyloheptane-2-one).

Preferably, the degradable material comprises 10-15 wt % of poly(butylenes-co-c-caprolactone carbonate) (PBCL) and 80-90 wt % of poly(lactic-co-glycolic acid) (PLGA), the poly(lactic-co-glycolic acid) is synthesized from PDLA (foscolic acid) and PGA (poly glycolic acid), and a molar ratio of the PLDA to PGA is 40:60. Preferably, the degradable material further comprises 1-5 wt % of sulfo-N-hydroxy succinimide sodium.

Preferably, the titanium screw is formed by helically buckling a wire made of titanium alloy.

Preferably, the titanium alloy comprises: 5.5-6.0 wt % of Mo, 1.5-2.0 wt % of Zr, 0.3-0.5 wt % of Mg, 0.05-0.15 wt % of Nb and a balance of Ti. The wire made of titanium alloy is performed by a micro-arc oxidation surface modification treatment, and electrolyte of the micro-arc oxidation surface modification treatment and an electrolyte solution comprises: 1.5-2.0 wt % of sodium citrate, 0.10-0.20 wt % of sodium borate, 0.05-0.10 wt % of glycine and a balance of water; wherein a voltage of the micro-arc oxidation surface modification treatment is at a range of 200-250V and a current density thereof is at a range of 0.02~0.20 Adm−2, and a treatment time is at a range of 10-20 min.

Compared with the conventional arts, the fixing device for soft tissue comprising the absorbable screw or the titanium of the present invention has beneficial effects as follows.

The fixing device for soft tissue comprising the absorbable screw or the titanium illustrated the present invention is particularly suitable for laparoscopic hernia repair operations. Furthermore, the fixing device of the present invention has characteristics of anti-adhesion, convenient and reliable operation. In the present invention, the catheter is a replacement element. After using, the catheter can be replaced in the fixing device for a repeated use.

DETAILED DESCRIPTION OF THE PREFERRED EMBODIMENT

Further description of a fixing device for soft tissue comprising an absorbable screw is illustrated combining with preferred embodiments of the present invention. These and other objectives, features, and advantages of the present invention will become apparent from the following detailed description, the accompanying drawings, and the appended claims.

Figure 1:
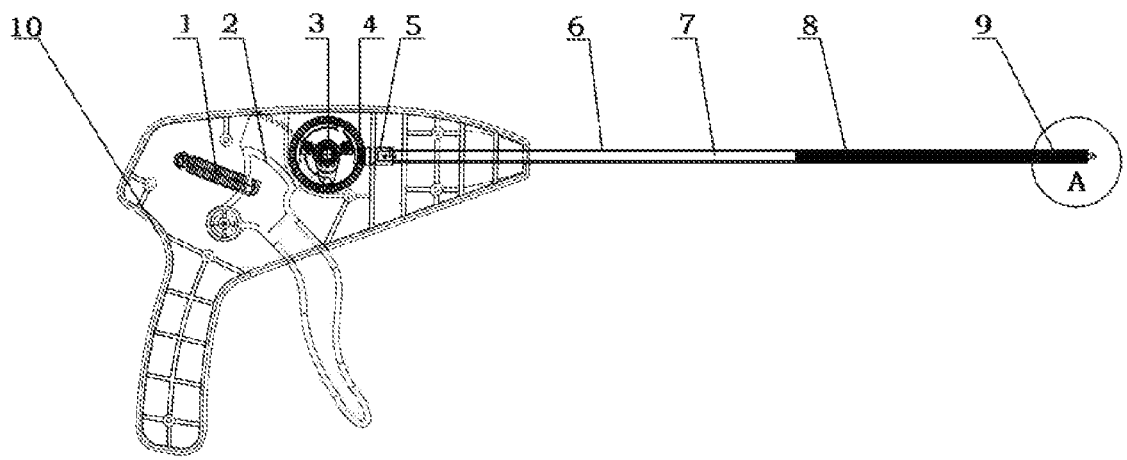
FIG. 1 is a sketch view of a fixing device for soft tissue according to a preferred embodiment of the present invention.
Figure 2:
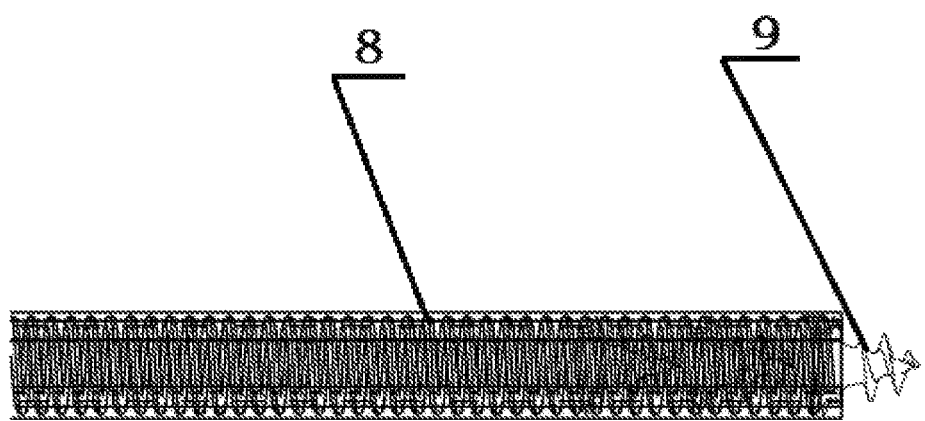
FIG. 2 is an enlarged structure view of an absorbable screw which is provided on a position of a circle A in the FIG. 1.
Figure 3:
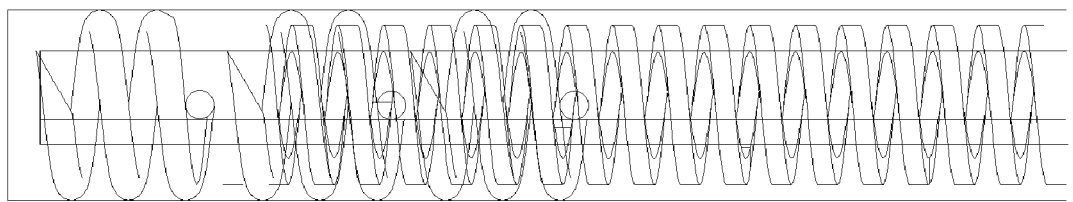
FIG. 3 is an enlarged structure view of a titanium screw which is provided on the position of the circle A in the FIG. 1.

Referring to FIGS. 1-2, according to a preferred embodiment of the present invention, a fixing device comprising an absorbable screw for soft tissue comprises:

a handle 10, an extension spring 1, a trigger 2, a driving gear 3, a large helical gear 4, a small helical gear 5, a screw tube 6 and a driving rod 7;

wherein a first end of the extension spring 1 is mounted on a fixing column on an internal wall of the handle 10, a second end of the extension spring 1 is provided on an upper end of the trigger 2, a first side of the upper end of the trigger 2 is rotatablely connected with an internal wall of the handle 10 via a rotation axis;

a helical gear matching with the driving gear 3 is provided on a second side of the upper end of the trigger 2, the trigger 2 extends from an inside out of the handle 10, in such a manner that a lower end of the trigger 2 is out of the handle 10;

the large helical gear 4 and the driving gear 3 are concentric, and the large helical gear 4 is driven by the driving gear 3, external teeth of the large helical gear 4 matches with external teeth of the small helical gear 5;

the driving rod 7 is driven by the rotation axis of the small helical gear 5, the screw tube 6 is sleeved on the driving rod 7, a first end of the screw tube 6 is provided inside the handle 10, and a second end of the screw tube 6 is provided out of the handle 10, a catheter 8 is connected on the second end of the screw pipe by threaded connection, and an absorbable screw 9 is provided inside the catheter 8, a screw thread is provided on a nailed beam of the absorbable screw 9, and a lead spring is provided on the screw thread.

Specifically, a plurality of the absorbable screws are connected in series and provided in a catheter, wherein heads of the absorbable screws face an outlet of the catheter. In the preferred embodiment, the trigger, the extension spring, the driving gear, the large helical gear, the small helical gear form a driving device of the fixing device for the soft tissue of the present invention. When used, by pulling the trigger, the driving rod is rotated driven by the driving device, in such a manner that the absorbable screw or the titanium screw can be shot out of the catheter one by one.

In the present invention, a lubricant coating is covered on the catheter, which is capable of facilitating sending the catheter of the fixing device for the soft tissue comprising the absorbable screw or the titanium screw into tissue of a human body smoothly, so as to prevent adhesion. In the conventional arts, the lubricant coating or the anti-adhesion is silicone oil, dimethyl silicone polymer or etc. In the present invention, a lubricant coating comprising Teflon is covered on the catheter, and a thickness of the lubricant coating is at a range of 3-5 μm. A surface hardness of the lubricant coating is at a range of Hv500-Hv1000, and a surface coefficient of friction is at a range of 0.1-0.05. The lubricant coating further comprises stable polymers selecting from a group consisting of: polymethyl methacrylate, polyacrylamide, polyacrylonitrile, polyether amide, Ethylenediamine, polycarbonate, polyketene, polyvinyl ether, polyvinyl ester, polyvinylpyrrolidone, polyethylene, polypropylene, polytetrafluoroethylene, polyolefin elastomer, polyisobutene, fluorosilicone, carboxymethyl chitosan, polyethylene terephthalate, poly-pentanoate, carboxymethyl cellulose, hydroxyethylcellulose, cellulose butyrate, cellulose acetate butyrate, ethyl-vinylacetate copolymer, chitosan and chitosan derivatives. Preferably, the lubricant coating comprises 0.01-1.5 wt % of antibacterial agent, wherein the antibacterial agent can be silver based antibacterial agent or non-silver based antibacterial agent. As an example of silver based antibacterial agent, the silver based antibacterial agent can be silver particles, silver based antibacterial agent or non-silver based antibacterial agent based on glass carriers, or silver based antibacterial agent based on zeolite carrier. The antibacterial agent can be added to a combination by a conventional mixing method and dispersed in a lubricating phase coating layer obtained by depositing. The antibacterial agent is capable of preventing or inhibiting growth of microorganisms carried, in such a manner that infection caused by fixing operation is prevented.

Embodiment 1

In the present invention, the absorbable screw is made of degradable material. As an example, the fixing device for soft tissue, as recited in claim 6, wherein the degradable material is selected from a group consisting of: poly(L-lactide), poly(D, L-lactide), poly(L-lactide-co-D, L-lactide), poly(D,L-lactide-co-glycolide), poly-glycolide, poly(L-lactide-co-glycolide), poly(glycolide-co-trimethylene carbonate), poly(L-lactide-co-trimethylene carbonate), poly(D,L-lactide-co-trimethylene carbonate), poly(L-lactide-co-caprolactone), poly (amino acids), poly (ε-caprolactone), poly (δ-valerolactone), poly (γ-butyrolactone), poly (β-hydroxybutyrate), poly(DL-lactide), poly(L-lactide), ethylene carbonate (1,3-dioxolan-2-one), propylene carbonate (4-methyl-1,3-dioxolan-2-one), 1,3-propylene carbonate (1,3-dioxan-2-one) and tetramethylene carbonate (1,3-dioxacyloheptane-2-one).

As an improvement, the degradable material comprises 10-15 wt % of poly(butylenes-co-ε-caprolactone carbonate) (PBCL) and 80-90 wt % of poly(lactic-co-glycolic acid) (PLGA), the poly(lactic-co-glycolic acid) is synthesized from PDLA (foscolic acid) and PGA (poly glycolic acid), wherein a molar ratio of the PDLA to the PGA is 40:60. Preferably, the degradable material further comprises 1-5 wt % of sulfo-N-hydroxy succinimide sodium. The static degradation testing based on Hanks' balanced salt solution indicates that: adding PBCL is capable of stabilizing a time which makes the degradable materials have a weight loss of 90% to be within 80-90 days. The degradation performance is excellent; the stimulation is small and the compatibility is excellent. Adding sulfo-N-hydroxy succinimide sodium is capable of facilitating hernia coalescence.

In the present invention, the absorbable screw is obtained by processes of raw material mixing, melt extruding and machining. As an example, raw material combination of the degradable materials is sent into a blender mixer to be evenly mixed, wherein a nixing temperature is controlled below 80° C. Mixed materials are cooled and then melt extruded by a single-screw extruder. Temperature on each section of the single-screw extruder is at a range of 150~210° C. Melt blending materials obtained are processed into a cylinder. A mechanic performance testing shows that a tensile strength of the cylinder is capable of reaching 50-60 MPa, and a bending strength thereof is capable of reaching 100-120 MPa. The stretched cylinder is cut into sections according by certain length, and then is performed with lathe processing according to screw thread parameters and screw structures, in such a manner that absorbable screw is obtained. In the present invention, the absorbable screw adopts a shape of the conventional bolts in the conventional art, e.g., a first half of the whole body is in a cone shape, and a second half thereof is in a cylinder shape, or the whole body is in a cone shape, so as to facilitate accurately positioning of the screw in the operation by a guide pin. Parameters of the screw thread are not limited and a deep and flattened thread is preferred.

Embodiment 2

In the Embodiment 2 of the present invention, the titanium screw is formed by helically buckling a wire made of titanium alloy. The titanium alloy comprises: 5.5-6.0 wt % of Mo, 1.5-2.0 wt % of Zr, 0.3-0.5 wt % of Mg, 0.05-0.15 wt % of Nb and a balance of Ti. By solution treatment, extension strength of the titanium alloy is capable of reaching 820-900 MPa, a yield strength is capable of reaching 800-850 MPa, an elongation is capable of reaching 25-35% and a fracture toughness is capable of reaching 85-90 MPam$^{-1/2}$, and thus malleability and toughness is good. During machining process, the wire made of titanium alloy is performed by a micro-arc oxidation surface modification treatment and an electrolyte of the micro-arc oxidation surface modification treatment, and an electrolyte solution comprises: 1.5-2.0 wt % of sodium citrate, 0.10-0.20 wt % of sodium borate, 0.05-0.10 wt % of glycine and a balance of water. After the modification treatment, adding an appropriate amount of Mg and Zr to alloy wire, and in a test of Hank's solution, a anodizing curve is capable of maintaining a stable sodium citrate at a voltage of 0.5-2.5V. A dissolution quantity of metallic ion is small (100 ppmcm$^{-2}$ below), which significantly improves corrosion resistance and biocompatibility of the titanium screw. Specifically, a voltage of the micro-arc oxidation surface modification treatment is at a range of 200-250V and a current density thereof is at a range of 0.02-0.20 Adm−2, and treatment time is at a range of 10-20 min.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A fixing device for soft tissue, comprising: a handle, an extension spring, a trigger, a driving gear, a large helical gear, a small helical gear, a screw tube and a driving rod;
    wherein a first end of the extension spring is mounted on an internal wall of the handle, a second end of the extension spring is provided on an upper end of the trigger, a first side of the upper end of the trigger is rotatablely connected with an internal wall of the handle via a rotation axis;
    a helical gear matching with the driving gear is provided on a second side of the upper end of the trigger, the trigger extends from an inside out of the handle, in such a manner that a lower end of the trigger is out of the handle;
    the large helical gear and the driving gear are concentric, and the large helical gear is driven by the driving gear, external teeth of the large helical gear matches with external teeth of the small helical gear;
    the driving rod is driven by the rotation axis of the small helical gear, the screw tube is sleeved on the driving rod, a first end of the screw tube is provided inside the handle, and a second end of the screw tube is provided out of the handle, a catheter is connected on the second end of the screw tube by threaded connection, and an absorbable screw or a titanium screw is provided inside the catheter;
    wherein a lubricant coating comprising Teflon is covered on the catheter, and a thickness of the lubricant coating is at a range of 3-5 μm;
    a surface hardness of the lubricant coating is at a range of Hv500-Hv1000, and a surface coefficient of friction thereof is at a range of 0.1-0.05;
    wherein the lubricant coating further comprises stable polymers selected from a group consisting of: polymethyl methacrylate, polyacrylamide, polyacrylonitrile, polyether amide, ethylenediamine, polycarbonate, polyketene, polyvinyl ether, polyvinyl ester, polyvinylpyrrolidone, polyethylene, polypropylene, polytetrafluoroethylene, polyolefin elastomer, polyisobutene, fluorosilicone, carboxymethyl chitosan, polyethylene terephthalate, poly-pentanoate, carboxymethyl cellulose, hydroxyethylcellulose, cellulose butyrate, cellulose acetate butyrate, ethyl-vinylacetate copolymer, chitosan and chitosan derivatives;
    wherein the lubricant coating further comprises antibacterial agent;
    wherein the absorbable screw is made of degradable material;
    wherein the degradable material is selected from a group consisting of:
    poly(L-lactide), poly(D, L-lactide), poly(L-lactide-co-D, L-lactide), poly(D,L-lactide-co-glycolide), poly-glycolide, poly(L-lactide-co-glycolide), poly(glycolide-co-trimethylene carbonate), poly(L-lactide-co-trimethylene carbonate), poly(D,L-lactide-co-trimethylene carbonate), poly(L-lactide-co-caprolactone), poly (amino acids), poly (ε-caprolactone), poly (δ-valerolactone), poly (γ-butyrolactone), poly (β-hydroxybutyrate), poly(DL-lactide), poly(L-lactide), ethylene carbonate 1,3-dioxolan-2-one), propylene carbonate (4-methyl-1,3-dioxolan-2-one), 1,3-propylene carbonate (1,3-dioxan-2-one) and tetramcthylene carbonate 1,3-dioxacyloheptane-2-one);
    wherein the titanium screw is formed by helically buckling a wire made of titanium alloy;
    wherein the titanium alloy comprises: 5.5-6.0 wt % of Mo, 1.5-2.0 wt % of Zr, 0.3-0.5 wt % of Mg, 0.05-0.15 wt % of Nb and a balance of Ti.

* * * * *